(12) United States Patent
Arnoux et al.

(10) Patent No.: US 9,468,286 B2
(45) Date of Patent: Oct. 18, 2016

(54) TOOTHBRUSH APPARATUS HAVING MULTIPLE ROTATABLE BRUSHING SYSTEMS

(71) Applicants: Patrick Arnoux, Marseilles (FR); Jean-Christophe Ferrer, Verrieres le Buisson (FR)

(72) Inventors: Patrick Arnoux, Marseilles (FR); Jean-Christophe Ferrer, Verrieres le Buisson (FR)

( * ) Notice: Subject to any disclaimer, the term of this patent is extended or adjusted under 35 U.S.C. 154(b) by 0 days.

(21) Appl. No.: 14/359,466

(22) PCT Filed: Nov. 16, 2012

(86) PCT No.: PCT/FR2012/052645
§ 371 (c)(1),
(2) Date: May 20, 2014

(87) PCT Pub. No.: WO2013/076408
PCT Pub. Date: May 30, 2013

(65) Prior Publication Data
US 2014/0325771 A1    Nov. 6, 2014

(30) Foreign Application Priority Data

Nov. 21, 2011    (FR) ...................................... 11 60575

(51) Int. Cl.
*A61C 17/26* (2006.01)
*A46B 13/02* (2006.01)
(Continued)

(52) U.S. Cl.
CPC ............. *A46B 9/045* (2013.01); *A46B 13/001* (2013.01); *A46B 13/02* (2013.01); *A61C 17/26* (2013.01)

(58) Field of Classification Search
CPC ...... A61C 17/22; A61C 17/26; A46B 9/045; A46B 13/001; A46B 13/02
See application file for complete search history.

(56) References Cited

U.S. PATENT DOCUMENTS 2,583,886 A * 1/1952 Schlegel ........................... 15/23
4,275,749 A * 6/1981 Caroli ............................... 15/23
(Continued)

FOREIGN PATENT DOCUMENTS

| EP | 0108097 A1 | 5/1984 |
| EP | 0488971 A2 | 6/1992 |
| EP | 0725602 A1 | 8/1996 |
| FR | 2489120 A1 | 3/1982 |

(Continued)

OTHER PUBLICATIONS

International Search Report and Written Opinion mailed Feb. 7, 2013 by the European Patent Office in counterpart application No. PCT/FR2012/052645.

*Primary Examiner* — Laura C Guidotti
(74) *Attorney, Agent, or Firm* — Abelman, Frayne & Schwab

(57) ABSTRACT

The present invention relates to a toothbrush apparatus having multiple rotatable brushing systems, including a body onto which a head (1) is attached, wherein said head is provided with adjacent counter-rotating brushes (2, 2') having an overall cylindrical outer shape and longitudinal axes that parallel to one another, each brush (2, 2') being rotated by a shaft (4, 4') and supported at each of the ends thereof by a bearing (3, 3', 5, 5') forming part of a holder (6) which defines the distance between the longitudinal axes of said brushes, said holder (6) including at least two flexible arms (6a, 6b, 6c, 6d) oriented substantially perpendicular to said longitudinal axes, such that the respective ends thereof form said bearings, said flexible arms being connected to a base (6e) capable of ensuring the attachment of said holder (6) onto the head (1). According to the invention, the apparatus further includes a flexible element (9, 9') partially surrounding at least one of said brushes (2), which is integrally produced with said holder (6).

2 Claims, 2 Drawing Sheets

(51) Int. Cl.
 *A46B 9/04* (2006.01)
 *A46B 13/00* (2006.01)

(56) References Cited

U.S. PATENT DOCUMENTS

| | | | |
|---|---|---|---|
| 5,794,296 A * | 8/1998 | Wong | 15/23 |
| 5,864,911 A | 2/1999 | Arnoux et al. | |
| 8,448,283 B2 | 5/2013 | Caville et al. | |

FOREIGN PATENT DOCUMENTS

| | | |
|---|---|---|
| FR | 2662598 A1 | 12/1991 |
| FR | 2926211 A1 | 1/2008 |
| FR | 2926210 A1 | 7/2009 |
| WO | WO83/03956 | 11/1983 |
| WO | WO95/11636 | 5/1995 |
| WO | WO2009/092957 A2 | 7/2009 |
| WO | WO2009/092958 | 7/2009 |

* cited by examiner

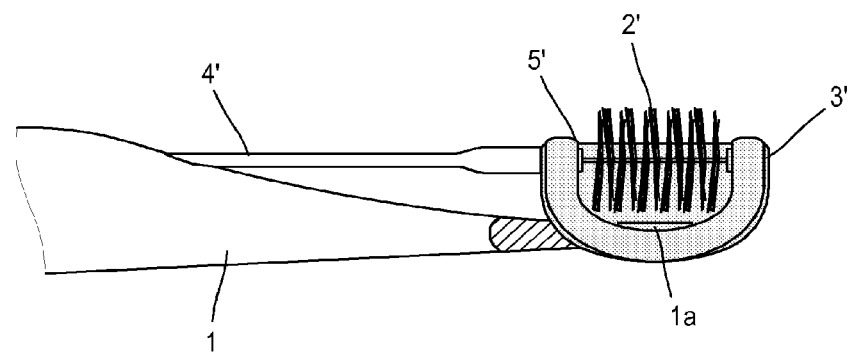
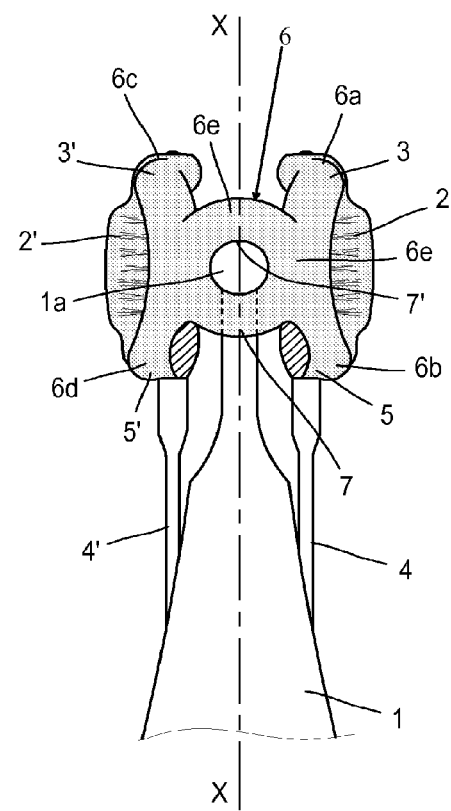

TOOTHBRUSH APPARATUS HAVING MULTIPLE ROTATABLE BRUSHING SYSTEMS

CROSS-REFERENCE TO RELATED APPLICATIONS

This is a 371 of PCT application no. PCT/FR2012/052645, filed 16 Nov. 2012, which claims priority to French patent application no. FR1160575, filed 21 Nov. 2011, the disclosures of which are incorporated herein by reference in their entirety and made a part of this application.

TECHNICAL FIELD OF THE INVENTION

The invention relates to the field of oral hygiene and more particularly to toothbrush apparatuses having several rotatable brushing systems. The invention can possibly relate to a use for animals.

In any case this involves carrying out a particular brushing of the teeth, more precisely a brushing from the gum towards the extremity of the teeth i.e. from the top downwards for the upper teeth and from the bottom upwards for the lower teeth. This type of brushing has shown to be the most effective for some time now.

PRIOR ART

As such documents describe toothbrushes with multiples rotatable brushing systems. 'Rotatable brushing system' means a brush or stembrush of cylindrical outer shape and formed of bristles oriented radially, or perpendicular to its longitudinal axis.

Document EP 0108097 B1 proposes an electric toothbrush comprising at least two rotating brushes of which the axes of rotation are parallel to one another. A mechanism placed in the handle of the toothbrush provides a counter-rotating of the brushes. Moreover several removable modules holding brushes can be adapted to the handle, according to the needs for use. A rigid cover surrounding the brushes is furthermore provided on the front portion of the system that is fastened in a removable manner (by clipping) onto the rear portion of the system. Such a toothbrush, constituted of several parts that can be adapted to one another, is therefore relatively complex to manufacture and can be fragile during use.

Application FR 2662598 A1 is also known which discloses a rotating toothbrush, for the simultaneous brushing inside and outside of the teeth. This toothbrush apparatus comprises two brushes with parallel axes of rotation and able to rotate in opposite direction. In addition the brushes are provided with rounded fairings on their ends, arranged on the outer surfaces of each brush. These fairings prevent the tongue and the inside of the cheek from being rubbed by the brushes, and therefore irritated. However these fairings are here additional rigid parts that can be broken and be damaged in contact with the teeth or following an abrupt movement of the toothbrush apparatus in the mouth of the user. The greatest danger is that the fairing breaks and that a small piece is swallowed by the user.

In the same field, one knows patent application EP 0488971 A2 that describes a toothbrush apparatus with two counter-rotating brushes partially surrounded by a cover forming a part of the end supporting the two brushes. Here again there is a rigid protective element, of complex shape, which therefore renders the manufacture not easy. Of course the same disadvantages as those mentioned hereinabove are present here.

Prior art further comprises document FR 2489120 which shows a toothbrush of the same type as those that have just been described, and of which the two brushes are partially masked by an outer screen arranged opposite the zone, located between the two brushes, where the teeth take up space. The outer screen can be comprised of two demi-cylinders or of semi-oval shape that covers the two brushes. Again, this screen shows a rigid and fragile part, which can be broken in the mouth of the user. In addition, such a part presents additional encumbrance that is not necessarily pleasant for the user.

A fairing of the same type is described in patent EP 0725602 B1 wherein consequently the same disadvantages are present.

DESCRIPTION OF THE INVENTION

The invention aims to overcome the disadvantages of prior art and in particular provide a toothbrush apparatus of which the brushes are partially covered with a protective element aiming to decrease the projections of particles or other elements directly in the mouth of the user. Of course the protective element avoids direct contact of the brush or brushes with the tongue or the inside of the cheek of the user.

To do this, according to the invention, a toothbrush apparatus having multiple rotatable brushing systems is proposed, comprising a body whereon is attached a head provided with adjacent counter-rotating brushes, of overall cylindrical outer shape, with longitudinal axes parallel to one another, with each brush being driven in rotation by a shaft and supported at each of its ends by a bearing forming part of a holder which determines the distance between the longitudinal axes of said brushes, said holder comprising at least two flexible arms oriented substantially perpendicular to said longitudinal axes of said brushes, in such a way that their respective ends constitute said bearings, said flexible arms being connected to a base able to provide for the fastening of said holder onto the head.

According to a first aspect, the apparatus further comprises a flexible element partially surrounding at least one of said brushes; this flexible element is advantageously integrally formed with said holder.

This characteristic increases the comfort for the user who as such does not perceive a rigid or sharp part in his mouth. Moreover and as shall be specified later on the flexible element is easy to manufacture since it is preferentially integrally moulded with the holder of the brush or brushes.

According to a preferred embodiment, the flexible element partially surrounds each of said brushes.

Particularly advantageously, the flexible element has a semi-cylindrical shape arranged at a constant distance from the outer cylindrical surface of at least one of said brushes. The flexible element constitutes to some extent a second skin around the brush or brushes, which is well tolerated by the user.

Preferably, said flexible element covers between one-third and one-half of the outer surface of at least one of said brushes.

Advantageously, said flexible element is made from a thermoplastic elastomere material.

Interestingly, said flexible element has a hardness between 20 and 35 shore D.

Moreover, said flexible element has an elasticity module between 10 and 30 MPa.

Preferably, said flexible element is made from Pebax®. And it has an average thickness of a magnitude of a few µm.

Advantageously, the flexible element and the holder are manufactured via extrusion.

The characteristic elements, non-restricted, mentioned hereinabove allow for easy and inexpensive manufacture; they provide a perfect tolerance on the part of the user; such a flexible element does not of course have the aforementioned disadvantages relating to prior art. In particular it cannot be broken in the mouth of the user.

The choice of material comprising the flexible element and the holder is unexpected because usually this material is used in the food field, for example to form food utensils or containers.

BRIEF DESCRIPTION OF THE FIGURES

Other characteristics, details and advantages of the invention shall appear when reading the following description, in reference to the annexed figures, which show:

FIG. 1, a longitudinal cross-section view of a toothbrush apparatus according to a first embodiment of the invention;

FIG. 2, a bottom view of a toothbrush apparatus according to the first embodiment of the invention;

For increased clarity, identical or similar elements are marked with identical reference signs in all of the figures.

DETAILED DESCRIPTION OF AN EMBODIMENT

Figure 3:
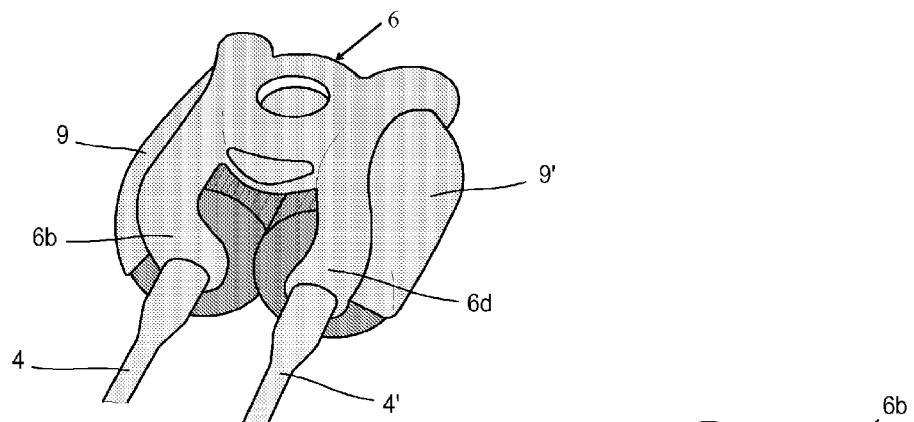
FIG. 3, a rear-bottom perspective of a toothbrush apparatus according to the first embodiment of the invention.

As can be seen in particular in FIGS. 1 and 2, the toothbrush apparatus according to the invention comprises a head 1 that can be connected, disconnected with regards to a body, not shown. The head 1 is provided at its end with two rotatable brushes 2, 2' of cylindrical outer shape, adjacent and longitudinal axes parallel to one another and parallel to the longitudinal axis XX of the head 1.

The brushes are advantageously driven in rotation, in a counter-rotating manner, by a mechanism not shown and known in itself which therefore shall not be described any further.

The brushes are supported at each of their ends by a bearing; two proximal bearings 5, 5' and two distal bearings 3, 3' are therefore provided; the bearings form part and/or are mounted on a holder 6 allowing for the relative positioning of the brushes 2, 2'. According to a preferred embodiment of the invention, the holder 6 comprises four flexible arms 6a, 6b, 6c, 6d positioned around a central part 6e used for the fastening of said holder 6 onto the head 1. The arms are substantially parallel to one another, and perpendicular to the axis XX. The fastening of the holder 6 onto the head 1 can be carried out as described in application FR 2926210, using two orifices, respectively 7 and 7', with axes perpendicular to one another; the first orifice 7 is coaxial with the axis XX of the head 1; the second orifice 7' has an axis substantially parallel to the arms 6a, 6b, 6c and 6d and allows for the snap-fitting of the holder 6 onto the head 1, more precisely on a stud 1a formed at the distal end of the head 1.

Figure 4:
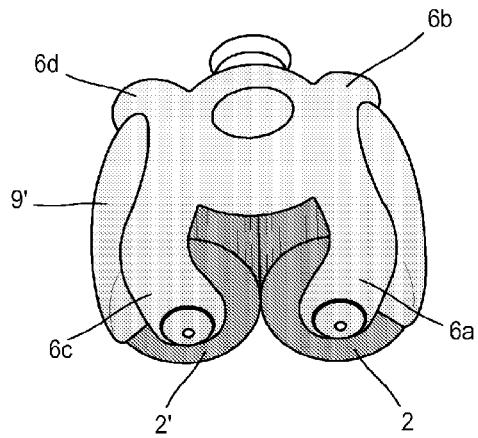
FIG. 4, a front-perspective of a toothbrush apparatus according to the first embodiment of the invention.
Figure 5:
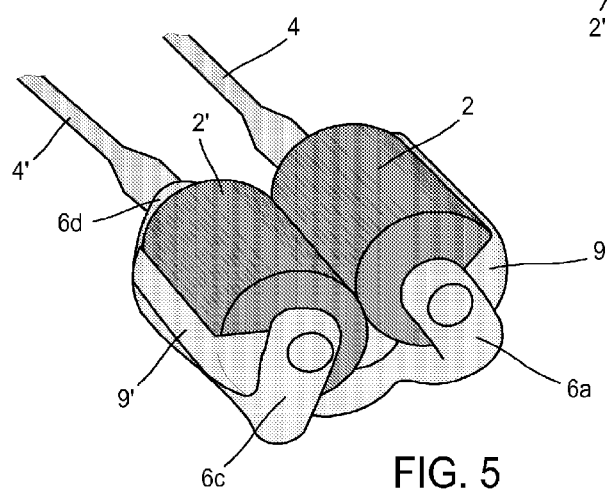
FIG. 5, another front-perspective of a toothbrush apparatus according to the first embodiment of the invention.

As can be seen more particularly in FIGS. 3 to 5, forming part of holder 6, a flexible element 9, 9' is provided, which partially surrounds at least one of the two brushes 2, 2'. The flexible element 9, 9' has an overall semi-cylindrical shape and is arranged at a short distance, a few mm, from the outer surface of the brush or brushes 2, 2'. This element 9, 9' forms a sort of protective veil around at least one brush 2, 2', more preferably around two brushes. The flexible element 9, 9' takes its support on each of the flexible but rigid arms 6a, 6b, 6c, 6d and it is shaped to partially surround at least one of said brushes 2, 2'. It covers between one-third and one-half of at least one of said brushes 2, 2'.

In order to manufacture effectively and easily such an element 9, a thermoplastic elastomere material is chosen. Preferably and with positive experience Pebax® marketed by the company Arkéma, is used. This material is flexible when it is stretched in the form of film as is the case in this invention. More precisely an elastomere of the Pebax® 3533 SA 01 or 2533 SA 01 type is preferred.

The average thickness of the element 9, 9' is of a magnitude of a few µm or even more, with an elasticity model between approximately 10 and 30 MPa. A hardness between 20 and 35 shore D is chosen. Its porosity allows for excellent permeability while still offering a barrier to water and bacteria.

With such characteristics the element 9, 9' therefore forms a flexible veil that covers at least one brush 2, 2'. This veil is perfectly tolerated by the user and it of course prevents any friction of at least one of the brushes with the inside of the cheek, the tongue and/or the gums of the user. Advantageously the veil allows the user to press for example with the tongue or the muscles of the cheeks, directly on the veil, without becoming injured; this increases the pressure on the teeth without any discomfort or hindrance for the user. A better brushing is therefore obtained.

Moreover the element 9, 9' being single-block with the holder 6 this unit is not very fragile and resists well to forces, vibrations and shaking created by the rotation of the brushes as well as by the contact with the teeth.

This unit formed by the holder 6 and the elements 9, 9' is manufactured in a simple manner, via a conventional and suitable manner of extrusion. The parameters for manufacturing are chosen by those skilled in the art.

The invention claimed is:

1. Toothbrush apparatus having multiple rotatable brushing systems, comprising a body whereon is attached a head (1) provided with adjacent counter-rotating brushes (2, 2'), of overall cylindrical outer shape, with longitudinal axes parallel to one another, with each brush (2, 2') being driven in rotation by a shaft (4, 4') and supported at each of its ends by a bearing (3, 3', 5, 5') forming part of a holder (6) which determines the distance between the longitudinal axes of said brushes, said holder (6) comprising at least two flexible arms (6a, 6b, 6c, 6d) oriented substantially perpendicular to said longitudinal axes, in such a way that their respective ends constitute said bearings, said flexible arms being connected to a base (6e) able to provide for the fastening of said holder (6) onto the head (1) wherein said holder further comprises a flexible element (9, 9') partially surrounding at least one of said brushes (2), wherein said flexible element is made from a thermoplastic elastomere material that has a hardness between 20 and 35 shore D, wherein said flexible element is integrally formed with said holder (6) and partially surrounds each of said brushes (2, 2'), wherein said flexible element (9, 9') has a semi-cylindrical shape arranged at a constant distance of the cylindrical outer surface of at least one of said brushes, wherein said flexible element (9, 9') covers between one-third and one-half of the outer surface of at least one of said brushes, wherein said flexible element (9, 9') has an elasticity module between 10 and 30 MPa, wherein said flexible element (9, 9') is made from polyether block amide, and wherein said flexible element (9, 9') has an average thickness of a magnitude of a few μm (micrometers).

2. Toothbrush apparatus as claimed in claim 1, wherein the flexible element (9, 9') and the holder (6) are manufactured via extrusion.

* * * * *